(12) United States Patent
Lecuyer et al.

(10) Patent No.: US 9,642,582 B2
(45) Date of Patent: May 9, 2017

(54) SHIELD FOR PATIENT POSITIONING IN EXTRA-ORAL IMAGING

(75) Inventors: Yann Lecuyer, Paris (FR); Sylvie Bothorel, Paris (FR); Philippe Congy, Meaux (FR)

(73) Assignee: TROPHY, Marne la Vallee (FR)

( * ) Notice: Subject to any disclaimer, the term of this patent is extended or adjusted under 35 U.S.C. 154(b) by 161 days.

(21) Appl. No.: 14/131,458

(22) PCT Filed: Jul. 22, 2011

(86) PCT No.: PCT/IB2011/002435
§ 371 (c)(1),
(2), (4) Date: Jan. 21, 2014

(87) PCT Pub. No.: WO2013/014488
PCT Pub. Date: Jan. 31, 2013

(65) Prior Publication Data
US 2014/0147803 A1    May 29, 2014

(51) Int. Cl.
*A61B 6/04* (2006.01)
*A61B 6/10* (2006.01)
*A61B 6/14* (2006.01)

(52) U.S. Cl.
CPC ............... *A61B 6/107* (2013.01); *A61B 6/04* (2013.01); *A61B 6/14* (2013.01)

(58) Field of Classification Search
None
See application file for complete search history.

(56) References Cited

U.S. PATENT DOCUMENTS

| | | | | |
|---|---|---|---|---|
| 2,758,307 A | * | 8/1956 | Treiber | A61F 9/025 2/8.1 |
| 2,798,958 A | * | 7/1957 | Hudson | A61B 6/14 378/150 |
| 3,536,913 A | * | 10/1970 | Huchel | A61B 6/14 378/168 |
| 5,038,047 A | * | 8/1991 | Still | A61B 6/107 128/857 |
| 5,500,884 A | * | 3/1996 | Guenther | A61B 6/14 378/197 |
| 6,118,842 A | | 9/2000 | Arai et al. | |
| 6,829,326 B2 | | 12/2004 | Woods et al. | |
| 7,236,563 B2 | | 6/2007 | Sa et al. | |
| 7,424,091 B2 | | 9/2008 | Park et al. | |
| 7,469,032 B2 | | 12/2008 | Walker et al. | |

(Continued)

FOREIGN PATENT DOCUMENTS

DE    2454591    5/1976
DE    4301908    8/1994

(Continued)

OTHER PUBLICATIONS

International Search Report for International Application No. PCT/US2011/002435 mailed on Apr. 23, 2013, 3 pages.

*Primary Examiner* — Michael Logie

(57) ABSTRACT

A patient positioning apparatus for an extra-oral imaging system includes a mount for revolving an x-ray source and an imaging sensor panel about a patient's head and a substantially transparent shield suspended from the mount. The shield has a chin support coupled to the shield and comprises a chin rest and a bite element and a forehead support coupled to the shield and comprises a head rest.

18 Claims, 10 Drawing Sheets

(56) References Cited

U.S. PATENT DOCUMENTS

| | | | |
|---|---|---|---|
| 7,577,232 B2 | 8/2009 | Tachibana et al. | |
| 2003/0225407 A1* | 12/2003 | Estrada, Jr. | A61B 17/6416 606/54 |
| 2006/0227393 A1* | 10/2006 | Herloski | H04N 1/02815 358/509 |
| 2006/0227939 A1* | 10/2006 | Walker | A61B 6/04 378/208 |
| 2007/0030951 A1 | 2/2007 | Park et al. | |
| 2007/0080308 A1* | 4/2007 | Mousavi Yeganeh | G21F 3/00 250/515.1 |
| 2007/0183567 A1 | 8/2007 | Rotondo et al. | |
| 2009/0110152 A1* | 4/2009 | Manzke | A61B 6/4423 378/195 |
| 2009/0175409 A1* | 7/2009 | Stockl | A61B 6/04 378/38 |
| 2009/0196395 A1 | 8/2009 | Gregorio et al. | |
| 2010/0195786 A1 | 8/2010 | Ro et al. | |
| 2011/0142197 A1* | 6/2011 | Walker | A61B 6/08 378/38 |
| 2011/0158384 A1* | 6/2011 | Beekman | G01T 1/1648 378/37 |
| 2012/0114095 A1* | 5/2012 | Smith | A61B 6/025 378/20 |
| 2012/0163544 A1* | 6/2012 | Mizrahi | A61B 5/0422 378/98.2 |

FOREIGN PATENT DOCUMENTS

| | | |
|---|---|---|
| JP | S57-95111 U | 6/1982 |
| JP | 3028330 U | 9/1996 |
| JP | 2009-136363 A | 6/2009 |
| JP | 2009-536055 A | 10/2009 |

\* cited by examiner

SHIELD FOR PATIENT POSITIONING IN EXTRA-ORAL IMAGING

FIELD OF THE INVENTION

The invention relates generally to the field of extra-oral dental imaging and more particularly to apparatus and methods for supporting the patient's head during the imaging session.

BACKGROUND OF THE INVENTION

Radiological imaging is recognized to have significant value for the dental practitioner, helping to identify various problems and to validate other measurements and observations related to the patient's teeth and supporting structures. Among x-ray systems with particular promise for improving dental care is the extra-oral imaging apparatus that is capable of obtaining a contiguous panoramic radiograph of the patient showing the entire dentition of the jaw. To obtain this type of image, a radiation source and an imaging detector, maintained at a fixed distance from each other, synchronously revolve about the patient, taking a series of images by directing and detecting radiation that is directed through the patient at different angles of revolution.

Combination systems that provide both CT and panoramic x-ray imaging have been proposed. For example, U.S. Pat. No. 6,118,842 entitled "X-RAY IMAGING APPARATUS" to Arai et al. describes an X-ray imaging apparatus for both CT imaging and panoramic imaging. The apparatus includes an X-ray source, an X-ray detector for detecting X-rays having passed through the subject, and supporting means for supporting the X-ray source and the X-ray detector so that they are spatially opposed to each other across the subject; and mode switching means for switching between a CT mode and a panorama mode. To detect X-rays, one large area X-ray detector is used. The X-ray imaging apparatus can obtain both types of images by switching modes during the imaging session. However, the proposed imaging apparatus performs both CT and panoramic imaging using only one detector. This requires an expensive detector capable of carrying out both imaging functions in a satisfactory manner.

More recently, U.S. Pat. No. 7,236,563 entitled "COMBINED PANORAMIC AND COMPUTED TOMOGRAPHY PHOTOGRAPHING APPARATUS" to Sa et al. describes a combination system that allows both CT and panoramic imaging using two separate sensors or detectors. By way of example, FIG. 1 in the present application shows an embodiment of the Sa et al. '563 imaging system, a combined panoramic and CT imaging apparatus 40. A telescopic column 18 is adjustable for height of the subject. The patient 12 or other subject, shown in dotted outline, is positioned between an x-ray source 10 and an x-ray imaging sensor panel 20. X-ray imaging sensor panel 20 rotates on a rotatable mount 30 in order to position either a CT or a panoramic sensor 21 for obtaining the exposure. For CT imaging, CT sensor 21 is positioned behind the subject, relative to x-ray source 10. The operator rotates CT sensor 21 into this position as part of imaging setup. Similarly, the operator rotates panoramic sensor 21 into position behind the subject as part of the setup for a panoramic imaging session.

Another system combines CT, panoramic, and cephalometric imaging from a single apparatus. U.S. Pat. No. 7,424,091 entitled "COMBINED PANORAMIC, CT (COMPUTED TOMOGRAPHY) AND CEPHALOMETRIC PHOTOGRAPHING APPARATUS" to Park et al. describes such a system.

One problem common to such systems for extra-oral imaging relates to the need both to keep the subject motionless and to maintain the subject in exactly the same position for each image capture during the imaging session. The perspective view of FIG. 2 shows one type of patient stabilization apparatus in an extra-oral imaging apparatus 50 that is typical of such systems. A handle 52 is mounted on column 18, giving the patient a place to grip for steadily maintaining a position. A chin rest 54 provides a bite element 56 and guides 58 for holding the head still while x-ray source 10 and sensor panel 20 revolve about the patient.

While conventional solutions such as that shown in FIG. 2 have the supporting structures that perform the needed task of keeping the patient still and in a fixed position, however, there is room for improvement. One difficulty relates to the job of initial setup, placing the patient in position, with the proper settings for chin rest height, bite element position, and handle height. The technician must work from behind the patient for much of this adjustment with reduced visibility, having little room to see how the patient is situated. Further, the patient may rock forward or backward on the chin, even with the guiding and bite devices provided.

Still other problems with conventional solutions relate to setting the imaging apparatus to the proper height for the patient and supporting the patient's head at an appropriate angle for CBCT imaging. Conventional systems use a number of complex height detection and head alignment sensing devices, including low-power lasers for example, for achieving proper positioning of the apparatus relative to the patient's head and for positioning the head at a suitable angle. Complex sensing and detection systems of this type can be costly and difficult to implement, further complicating the job of the technician or practitioner.

Another difficulty relates to patient comfort. With the arrangement of FIG. 2, the patient must stand facing away from the dentist or technician. Patients report feeling trapped and uncomfortable with such an apparatus, as if locked in place during the imaging session.

Thus, there is a need for a patient support apparatus that allows easier setup by the technician and is less confining and intimidating to the patient.

SUMMARY OF THE INVENTION

An object of the present invention is to address the need for improvement for patient positioning and support during extra-oral imaging. With this object in mind, the present invention provides a patient positioning apparatus for an extra-oral imaging system, the apparatus comprising: a mount for revolving an x-ray source and an imaging sensor panel about a patient's head; and a substantially transparent shield suspended from the mount and comprising: a chin support that is coupled to the shield and comprises a chin rest and a bite element; and a forehead support that is coupled to the shield and comprises a head rest.

A feature of the present invention is the use of a substantially transparent shield that allows visibility of the patient for the practitioner and reduces patient discomfort.

An advantage of the present invention is its relative simplicity of design and adaptability to patient sizes. Simplicity of design and use of less expensive materials helps to provide a patient imaging apparatus that is reduced in cost over alternative devices used for this purpose.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
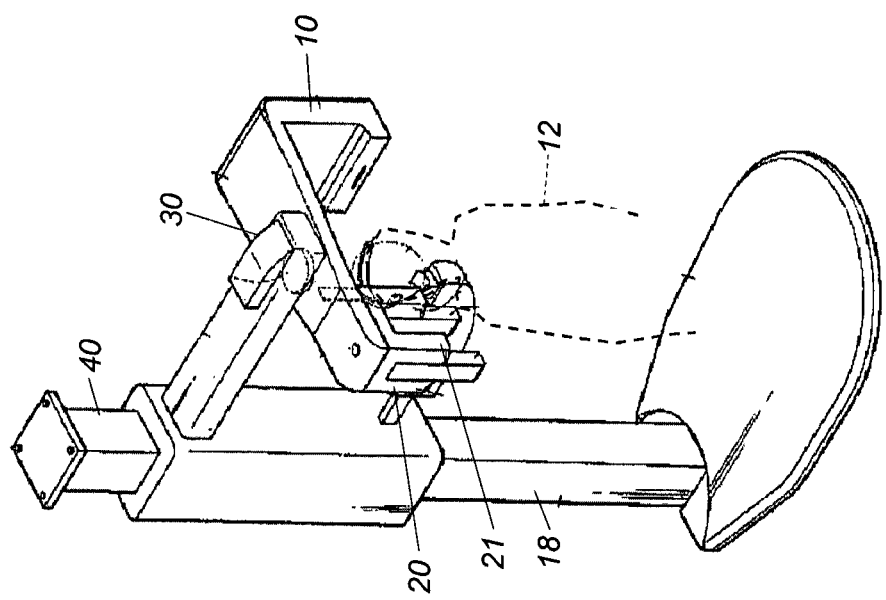
FIG. 1 is a perspective view of a prior art extra-oral imaging apparatus.
Figure 2:
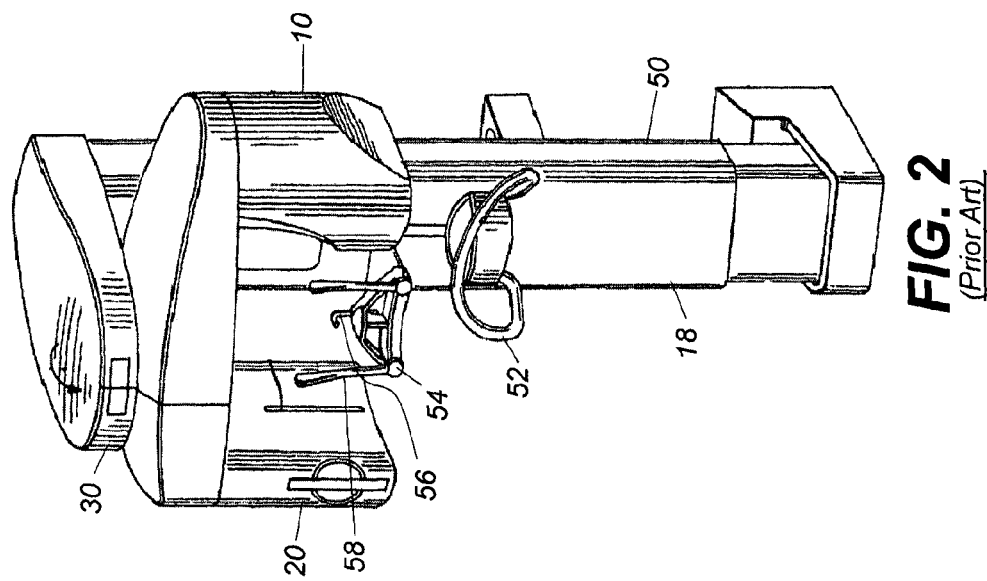
FIG. 2 is a perspective view showing prior art components for patient positioning and support in a conventional extra-oral imaging apparatus.

The following is a detailed description of the preferred embodiments of the invention, reference being made to the drawings in which the same reference numerals identify the same elements of structure in each of the several figures.

Where used, the terms "first", "second", and so on, do not necessarily denote any ordinal or priority relation, but may simply be used to more clearly distinguish one element from another.

Figure 3:
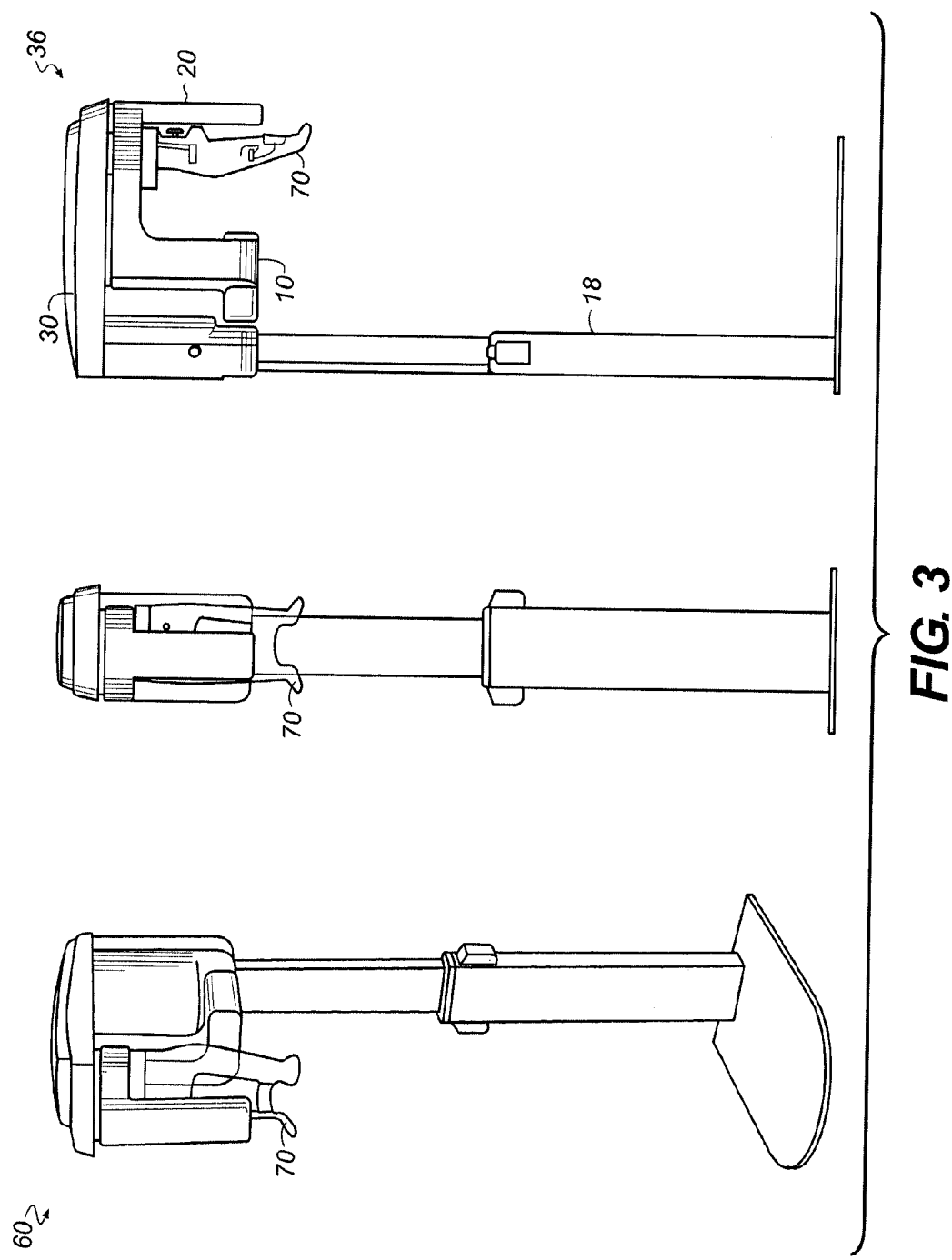
FIG. 3 shows perspective, front, and side views of an extra-oral imaging apparatus according to an embodiment of the present invention.

Embodiments of the present invention address the need for an improved patient support apparatus that is easy to use and more comfortable for the patient than existing devices. Referring to FIG. 3, there is shows an extra-oral imaging apparatus 60 that has mount 30 on column 18 with x-ray source 10 and x-ray sensor panel 20 energizable to revolve about the patient for obtaining CT and panoramic images of the patient. As part of a patient positioning apparatus 36, a substantially transparent patient-positioning shield 70 is suspended from mount 30, disposed for supporting the patient's head in place between source 10 and sensor panel 20. The vertical displacement of mount 30 is further adjustable to suit the height of the patient. To achieve this, the height of column 18 can be manually adjusted or can be controlled using a motor or other actuator, as described subsequently.

Figure 4:
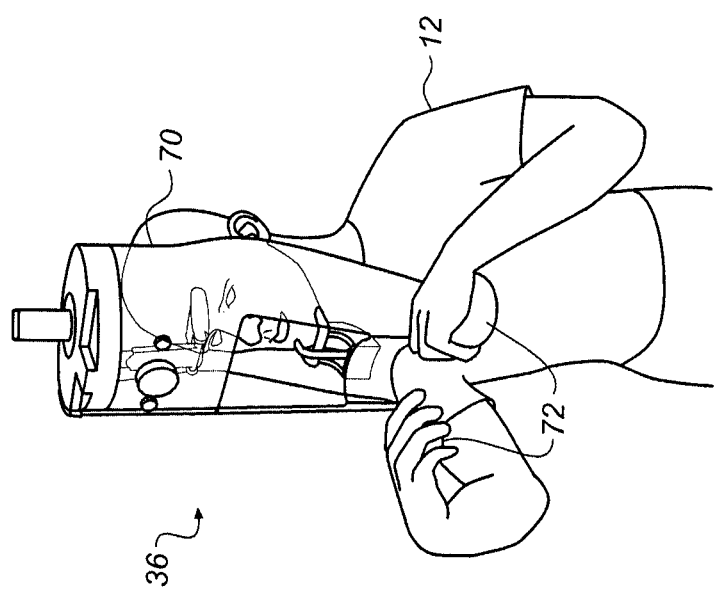
FIG. 4 shows a patient positioned using the open-faced shield of the present invention.

The perspective view of FIG. 4 shows the positioning of patient 12 using shield 70. Two handles 72 are provided on shield 70 itself, so that the patient's grip, tending to pull the head forward into shield 70, helps to stabilize head position. Shield 70 extends from mount 30, as was shown in FIG. 3. Advantageously, the patient faces outward when using shield 70, allowing the practitioner to communicate with the patient more easily and helping to reduce patient discomfort during the imaging session.

Figure 5:
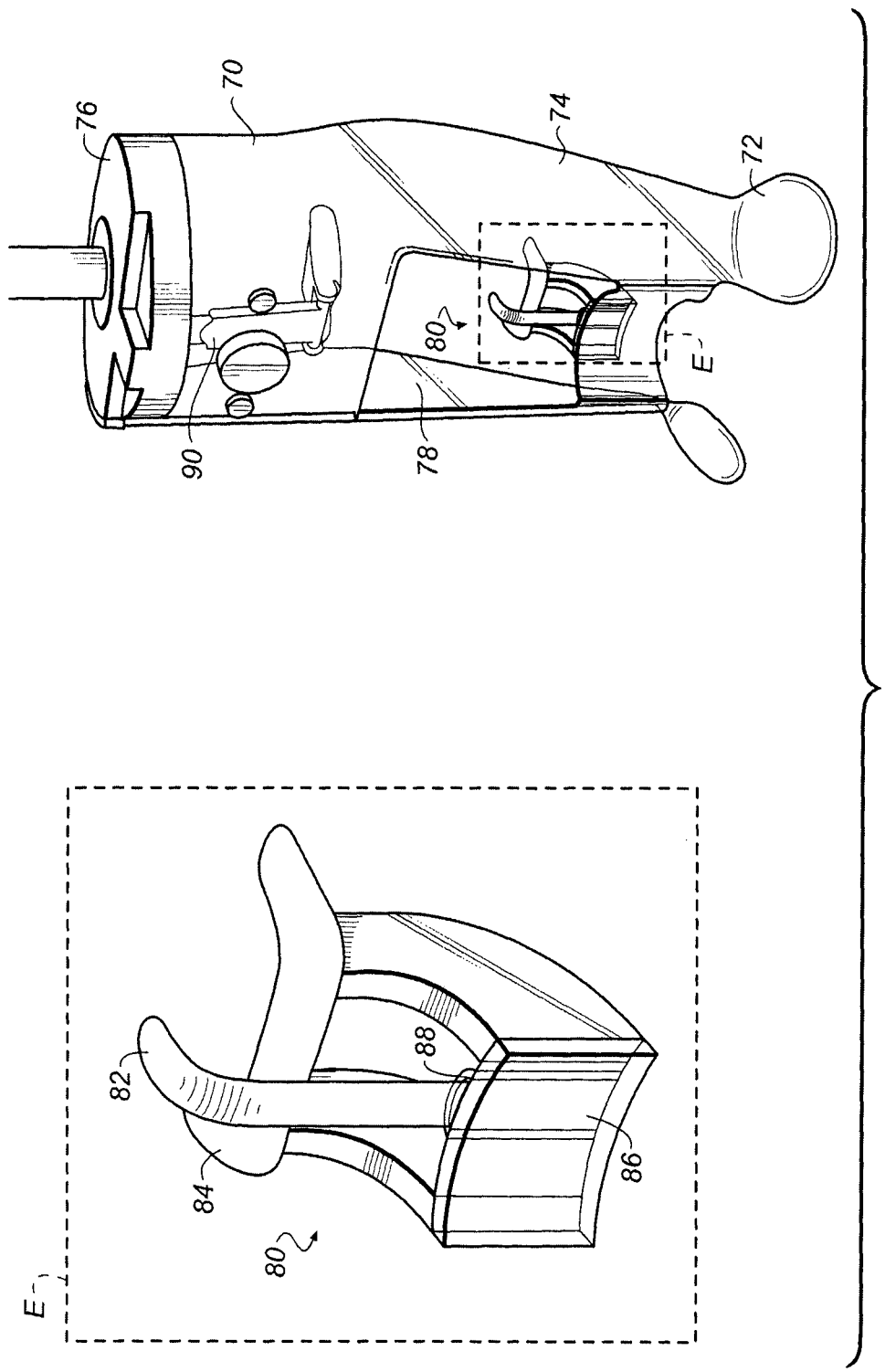
FIG. 5 is a perspective view of the open-faced shield of the present invention, showing details of the chin rest and bite element.

The perspective view of FIG. 5 shows features of shield 70 according to an embodiment of the present invention. A face plate 74 extends from a support 76. Face plate 74 is at least substantially transparent, allowing the patient to see outward, for a less captive feeling, and allowing better visibility of the patient for the technician who helps assist with patient setup. A material is considered to be substantially transparent when it transmits at least about 40 percent of visible light, preferably more than about 60 percent, more preferably more than about 80 percent of visible light. A higher amount of transparency to x-ray radiation is needed for imaging. The transparent material of shield 70 may have optional treatment to reduce glare or reflection, such as an anti-reflection coating, or may be tinted for appearance or for improved suitability to the patient. An open window 78 provides an opening that also helps to improve visibility in both directions. In one embodiment, face plate 74 is formed from a molded polycarbonate material that is substantially transparent to both x-ray radiation and visible light. In one embodiment, mask edges are further treated or shaped to reduce stripe artifacts in the x-ray image, such as by tapering edge thickness, for example.

Enlarged section E in FIG. 5 shows a chin support 80 which is removably installed along the inner or patient side of shield 70. Chin support 80 includes a chin rest 84 along with a bite element 82. A height adjuster 86 allows variable adjustment of the height of bite element 82, which can be slid to an appropriate position along a groove 88.

Figure 6:
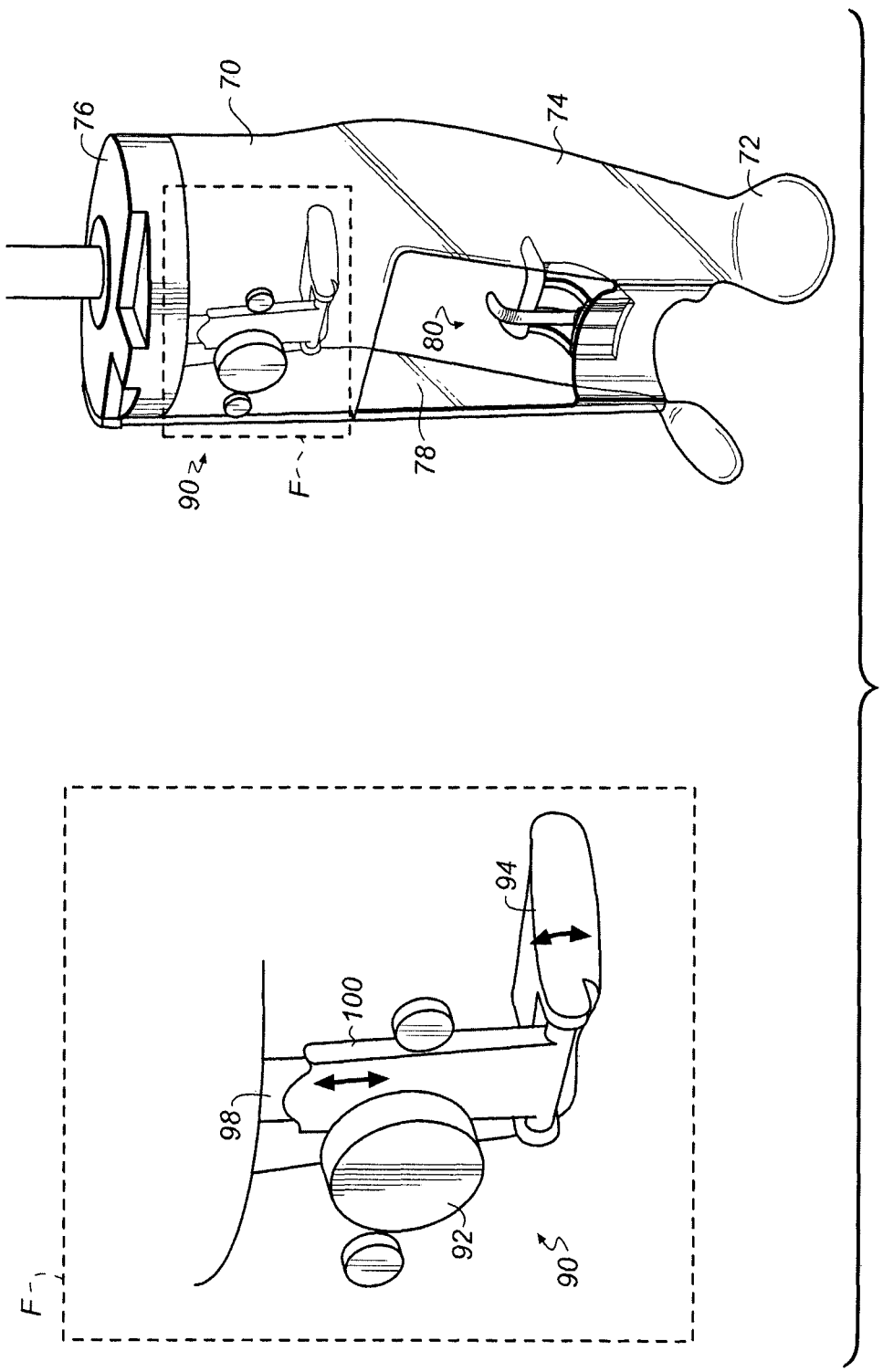
FIG. 6 is a perspective view of the open-faced shield of the present invention, showing details of the forehead support.

The perspective view of FIG. 6 shows additional features of shield 70. Enlarged section F shows a forehead support 90, also removably installed on the patient side of shield 70. An angle adjuster 92 allows adjustment of the front-to-back angular displacement of a head rest 94, against which the patient forehead is to lean. Vertical adjustment is obtained by sliding an extended member 100 of headrest 94 upward or downward within a sleeve 98. Head rest 94 is also horizontally rotatable to fit more comfortably against the forehead of the patient.

Figure 7:
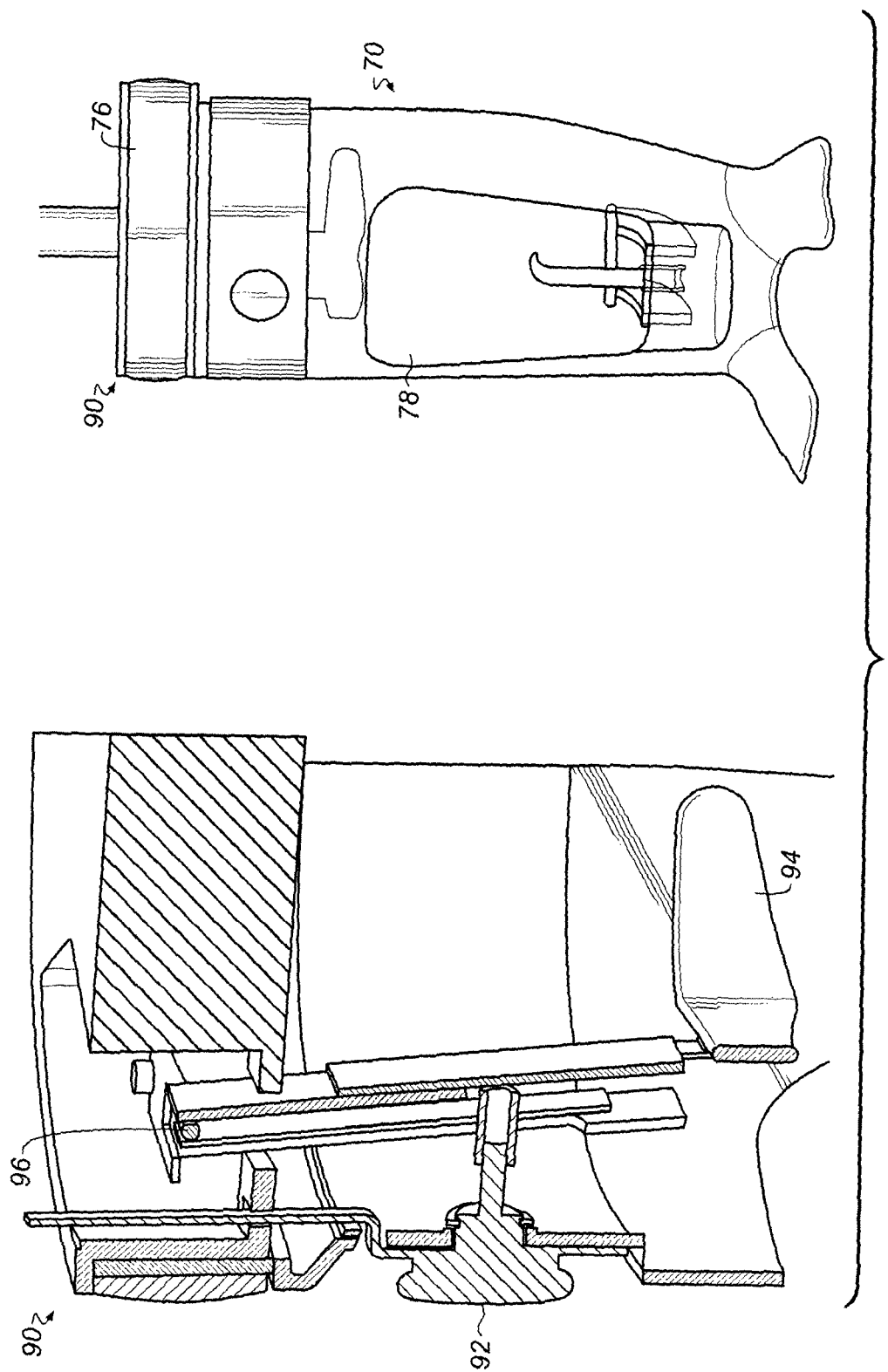
FIG. 7 is a perspective view that shows the mechanical arrangement of the forehead support according to an embodiment of the present invention.
Figure 8:
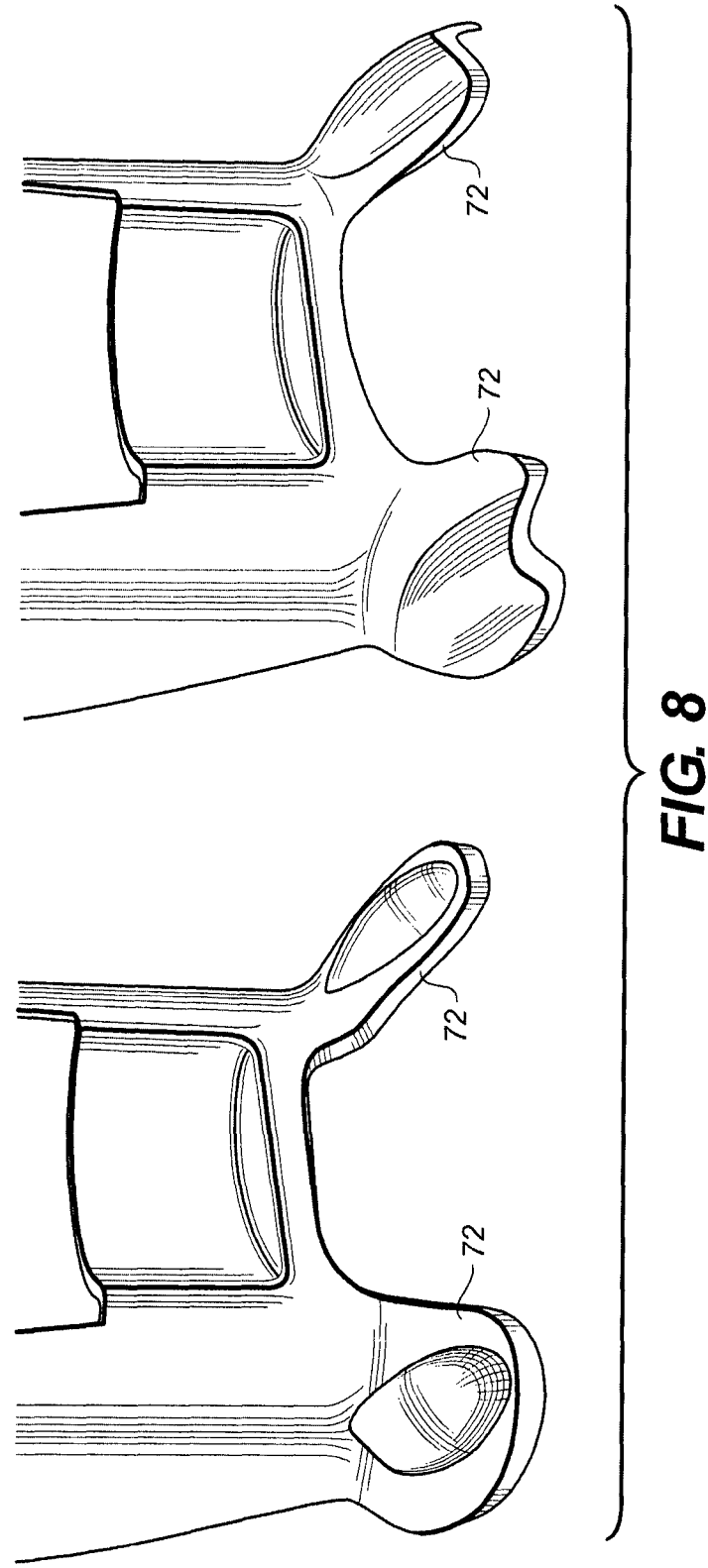
FIG. 8 is a perspective view showing alternate handle arrangements for the patient positioning shield of the present invention.

The perspective cross-section view of FIG. 7 shows a pivot 96 at the top of forehead support 90 in one embodiment. FIG. 8 shows different configurations for handles 72. Pivot 96 allows forehead support 90 to be in a more comfortable position against the patient.

Figure 9:
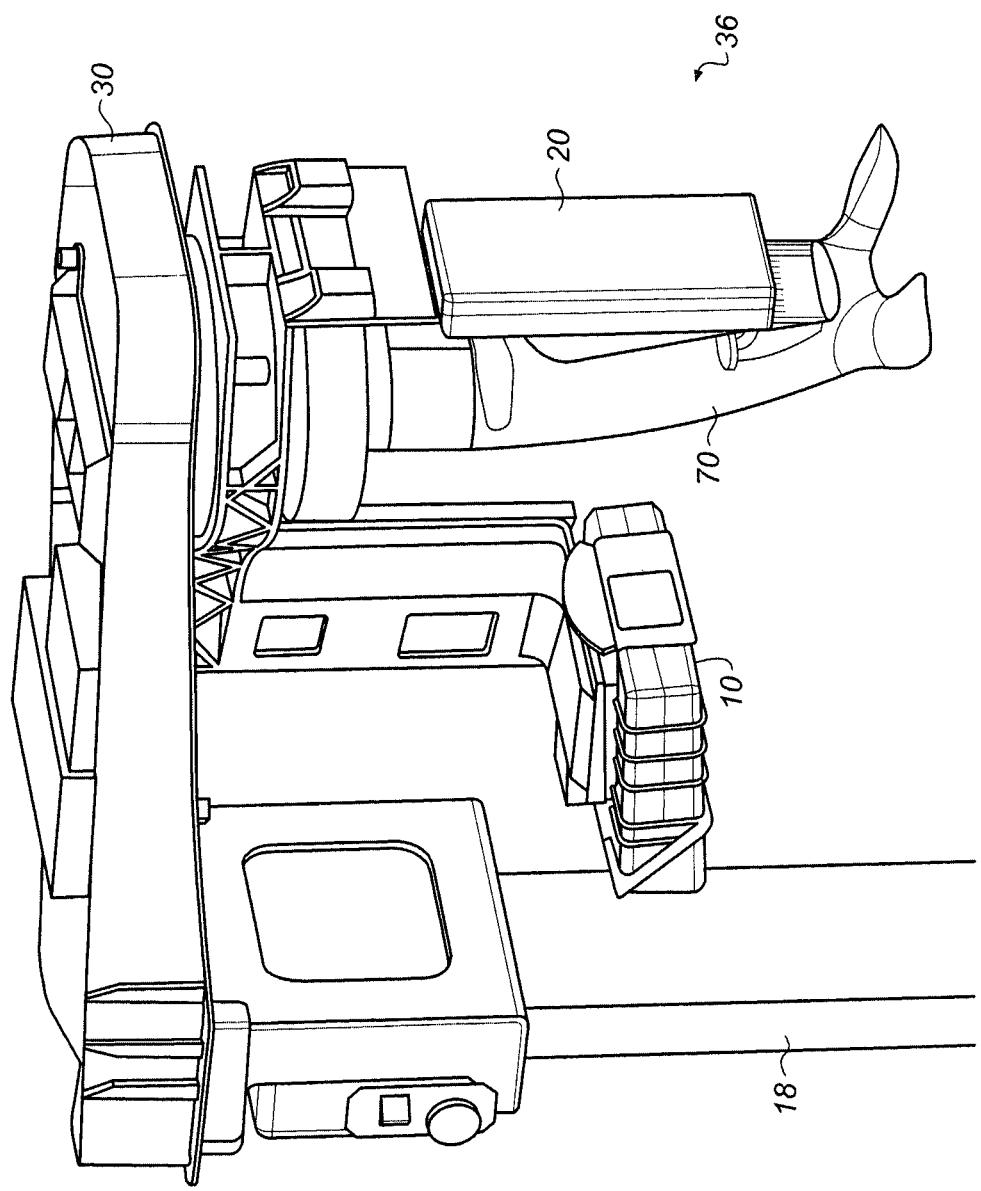
FIG. 9 is a perspective view that shows component arrangement for the revolving apparatus according to an embodiment of the present invention.

The perspective view of FIG. 9 shows the relationship of shield 70 to x-ray source 10 and sensor panel 20 components according to one embodiment of the patient positioning apparatus 36 of the present invention, with mount 30 shown without covers. Shield 70 stores against sensor panel 20 in the configuration shown, and rotates outward for positioning against the patient's chin.

Figure 10:
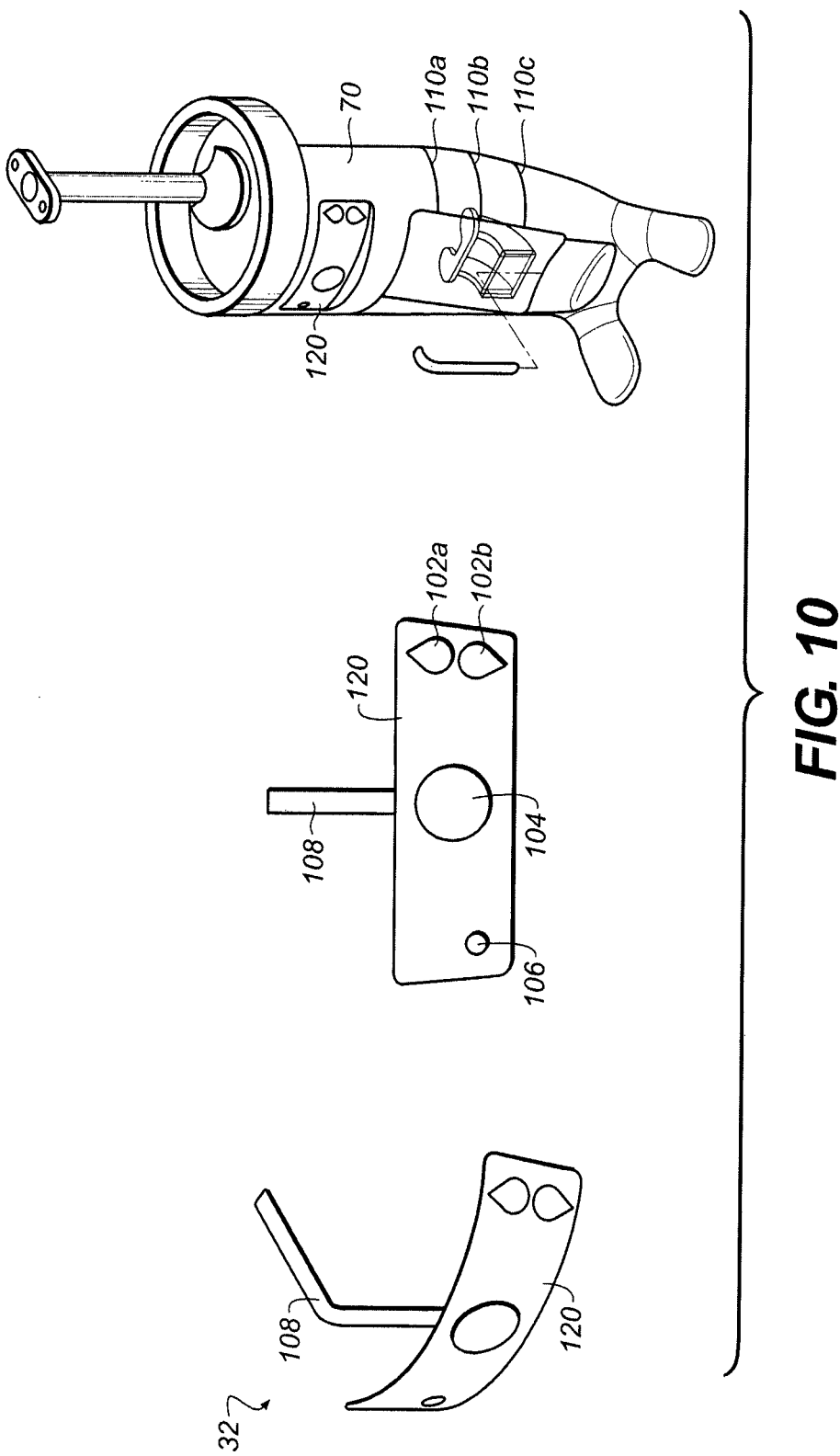
FIG. 10 is a perspective view that shows additional features for equipment setup and for positioning of the patient according to an embodiment of the present invention.

Referring to FIG. 3, column 18 supporting mount 30 is adjustable to an appropriate height for the patient. While the height can be manually set by the operator, it can be advantageous to use a motor or other type of actuator that can be energized to adjust column 18 height and thus adjust the vertical displacement of mount 30. The perspective view of FIG. 10 shows an optional control panel 120 that can be mounted on or otherwise coupled to shield 70 to allow operator adjustment of the column 18 height. Control panel 120 has a hole 104 for fitting over angle adjuster 92 (FIG. 6) to seat against the surface of shield 70. Controls 102*a* and 102*b* on control panel 120 enable the operator to adjust height upward or downward, respectively. Controls 102*a* and 102*b* are pushbuttons according to one embodiment of the present invention. An indicator 106, when energized, illuminates to show power status for the apparatus or for the column height adjustment components. Controls 102*a* and 102*b* communicate control signals to a height adjustment actuator 32 that is coupled to column 18 by means of a cable or other electrical connection 108, such as a wireless connection.

According to one embodiment of the present invention, control panel 120 is also formed of a transparent material, such as LEXAN™ polycarbonate resin thermoplastic from SABIC Innovative Plastics, Inc., The Netherlands. Other materials can alternately be used.

FIG. 10 also shows markings that help the operator to properly orient the patient's head so that the jaw is at the correct angle for imaging. One or more guide lines, shown as guide lines 110*a*, 110*b*, and 110*c* in the example of FIG. 10, are provided on shield 70 for such a purpose. According to one embodiment of the present invention, guide lines 110*a*, 110*b*, and 110*c* help the operator to horizontally align the dental arch to the ear of the patient. Guide lines or other markings can be printed on shield 70, such as by serigraphic printing, or may be etched or otherwise formed on or within the surface of shield 70.

While the invention has been described with reference to exemplary embodiments, it will be understood by those skilled in the art that various changes may be made and equivalents may be substituted for elements thereof without departing from the scope of the invention. Therefore, it is intended that the invention not be limited to the particular embodiment disclosed as the best mode contemplated for carrying out this invention, but that the invention will include all embodiments falling within the scope of the appended claims. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An extra-oral imaging system, comprising:
   a mount;
   a gantry movable coupled to the mount for revolving an x-ray source and an imaging sensor panel about a patient's head, the gantry extending between a first end mounting the x-ray source and a second opposing end mounting the imaging sensor panel; and
   a patient positioning apparatus suspended from the mount, comprising:
      a substantially transparent shield including a support;
      a chin support mounted to the inside of the shield and includes a chin rest and a bite element; and
      a forehead support mounted to the inside of the shield and includes a head rest, and where the support of the substantially transparent shield is used to attach the patient positioning apparatus to the mount and suspend the patient positioning apparatus from the mount through the gantry between the x-ray source and the imaging sensor panel.

2. The system of claim 1 further comprising an open window in the transparent shield completely disposed between the chin support and the forehead support to expose at least the bite element in the open window.

3. The system of claim 1, wherein the substantially transparent shield is formed from a molded polycarbonate material.

4. The system of claim 1, wherein the chin support further comprises a height adjuster for the bite element.

5. The system of claim 1, wherein the forehead support is connected to the substantially transparent shield, where the forehead support is configured to be adjustably pivotable relative to the transparent shield toward the patient using its connection to the substantially transparent shield.

6. The system of claim 1, wherein the shield further comprises one or more handles for gripping by the patient during imaging.

7. The system of claim 1, where the transparent shield extends between the chin support and the forehead support, where the transparent shield is positioned between the x-ray source and the imaging sensor panel, and wherein the shield further comprises one or more controls thereon for setting a column height adjustment for the mount.

8. The system of claim 7, wherein the one or more controls are mounted on a separate panel that is mounted on the shield.

9. The system of claim 1, wherein the shield further comprises one or more markings to assist in patient positioning.

10. A patient positioning apparatus for an extra-oral imaging system, the apparatus comprising:
    a mount for revolving an x-ray source and an imaging sensor panel about a patient's head; and
    a patient positioning apparatus suspended from the mount, comprising:
       a substantially transparent shield;
       a chin support coupled to the shield that includes a chin rest and a bite element;
       a forehead support coupled to the shield that includes a head rest;
       an open window in the substantially transparent shield between the chin support and the forehead support; and
       one or more controls are mounted to the shield for setting a column height adjustment for the mount at the shield.

11. The system of claim 10, wherein the chin support further comprises a height adjuster for the bite element.

12. The system of claim 10, wherein the forehead support is connected to the substantially transparent shield, where the forehead support is disposed to be adjustably pivotable relative to the transparent shield toward the patient using its connection to the substantially transparent shield.

13. The system of claim 10, wherein the shield further comprises one or more handles for gripping by the patient during imaging.

14. A method for positioning a patient for extra-oral imaging, the method comprising:
    providing a movable mount;
    providing a gantry, movably coupled to the mount, that extends between a first end mounting an x-ray source and a second opposing end mounting an imaging sensor panel for revolving about an imaging area for a patient's head; and suspending a patient positioning apparatus comprising an elongated patient cover from the mount, wherein the elongated patient cover comprises a chin support coupled to the elongated patient cover that includes a chin rest and a bite element, wherein the elongated patient cover comprises a forehead support coupled to the elongated patient cover that includes a head rest, and wherein the elongated patient cover comprises one or more controls mounted thereon for moving the gantry to a user selected column height.

15. The method of claim 14 further comprising providing the elongated patient cover with an open window in the elongated patient cover entirely disposed between the chin support and the forehead support.

16. The method of claim 14 wherein the forehead support is connected to the elongated patient cover, where the forehead support is disposed to be adjustably pivotable relative to the elongated patient cover toward the patient using its connection to the substantially transparent elongated patient cover.

17. The method of claim 14 wherein the patient positioning apparatus is suspended from the mount through the gantry using the elongated patient cover and supported by its attachment to the mount.

18. The method of claim 14 wherein the one or more controls for moving the gantry to a user selected column height by column height adjustment of the mount.

* * * * *